United States Patent
Katayama et al.

[11] Patent Number: 6,066,704
[45] Date of Patent: May 23, 2000

[54] TRANSITION METAL COMPLEX, CATALYST FOR OLEFIN POLYMERIZATION, AND PROCESS FOR PRODUCING OLEFIN POLYMERS

[75] Inventors: Hiroaki Katayama; Akio Imai, both of Ichihara; Hidenori Hanaoka, Osaka; Norio Kawamura, Chiba; Akira Miyashita, Ageo, all of Japan

[73] Assignee: Sumitomo Chemical Company, Limited, Osaka, Japan

[21] Appl. No.: 09/029,887

[22] PCT Filed: Aug. 30, 1996

[86] PCT No.: PCT/JP96/02439

§ 371 Date: Jun. 26, 1998

§ 102(e) Date: Jun. 26, 1998

[87] PCT Pub. No.: WO97/08179

PCT Pub. Date: Mar. 6, 1997

[30] Foreign Application Priority Data

Aug. 31, 1995 [JP] Japan ................... 7-224163

[51] Int. Cl.$^7$ ................ C08F 4/44; C07F 7/00; C07F 7/28; B01J 31/00; B01J 37/00
[52] U.S. Cl. .......... 526/127; 526/133; 526/134; 526/153; 526/160; 526/943; 556/12; 556/52; 502/103; 502/117; 502/118; 502/119; 502/123; 502/124; 502/125; 502/128
[58] Field of Search ........ 556/12, 52; 526/127, 526/153, 160; 502/103, 117, 118, 119, 123, 124, 125, 128

[56] References Cited

U.S. PATENT DOCUMENTS

| | | |
|---|---|---|
| 5,055,438 | 10/1991 | Canich . |
| 5,055,483 | 10/1991 | Ruger et al. . |
| 5,064,802 | 11/1991 | Stevens et al. . |
| 5,132,380 | 7/1992 | Stevens et al. . |
| 5,321,106 | 6/1994 | LaPointe . |
| 5,374,696 | 12/1994 | Rosen et al. .......... 526/160 |
| 5,637,660 | 6/1997 | Nagy et al. .......... 526/160 |
| 5,856,258 | 1/1999 | Marks et al. .......... 502/103 |
| 5,936,051 | 8/1999 | Santi et al. .......... 502/103 |

FOREIGN PATENT DOCUMENTS

| | | |
|---|---|---|
| 416 815 | 3/1991 | European Pat. Off. . |
| 3-188092 | 8/1991 | Japan . |
| 5-507756 | 11/1993 | Japan . |
| 92/00333 | 1/1992 | WIPO . |

OTHER PUBLICATIONS

J. Christoffers et al., Agnew. Chem. Int. Ed. Engl., vol. 34, No. 20, pp. 2266–2267, 1995.
J. Okuda, Comments Inorg. Chem., vol. 16, No. 4, pp. 185–205, 1994.
P. Jutzi et al., J. Organomet. Chem., vol. 500, pp. 175–185, 1995.
G. Trouve et al., J. Organomet. Chem., vol. 511, pp. 255–262, 1996.
A. van der Zeijden et al., Organometallics, vol. 16, No. 12, pp. 2651–2658, 1997.

*Primary Examiner*—Mark L. Bell
*Assistant Examiner*—J. Pasterczyk
*Attorney, Agent, or Firm*—Pillsbury Madison & Sutro LLP

[57] ABSTRACT

A transition metal complex represented by the formula [1]

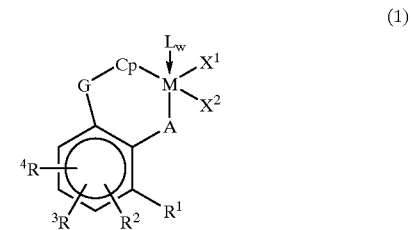

(1)

wherein M is a transition metal atom of the group 4 of the periodic table of elements; Cp is a group having a cyclopentadiene type anionic skeleton; A and G are each a divalent residue containing an atom of the group 15 or 16 of the periodic table of elements and may be the same with or different from each other; $X^1$, $X^2$, $R^1$, $R^2$, $R^3$ and $R^4$ are each independently a hydrogen atom, halogen atom, alkyl group with the number of carbon atoms of 1–20 optionally substituted with at least one halogen atom, aralkyl group with the number of carbon atoms of 7–20 optionally substituted with at least one halogen atom, aryl group with the number of carbon atoms of 6–20 optionally substituted with at least one halogen atom, substituted silyl group with the number of carbon atoms of 1–20 optionally substituted with at least one halogen atom, alkoxy group with the number of carbon atoms of 1–20 optionally substituted with at least one halogen atom, aralkyloxy group with the number of carbon atoms of 7–20 optionally substituted with at least one halogen atom, aryloxy group with the number of carbon atoms of 6–20 optionally substituted with at least one halogen atom or a di-substituted amino group with the number of carbon atoms of 2–20, provided that $R^1$, $R^2$, $R^3$ and $R^4$ may optionally combine with each other to form a ring; L is a Lewis base and w is an integer of 0–2, an olefin polymerization catalyst and a process for producing olefin polymers which uses the catalyst.

15 Claims, No Drawings

TRANSITION METAL COMPLEX, CATALYST FOR OLEFIN POLYMERIZATION, AND PROCESS FOR PRODUCING OLEFIN POLYMERS

This application is the national phase of international application PCT/JP96/02439 filed Aug. 30, 1996 which designated the U.S.

TECHNICAL FIELD

The present invention relates to a transition metal complex useful as an olefin polymerization catalyst component, an olefin polymerization catalyst and a process for producing olefin polymers. In more particular, it relates to a transition metal complex useful as an olefin polymerization catalyst component which has a ligand comprising an aromatic ring having a hetero atom in the substituent and a cyclopentadienyl ring linked with each other by a hetero atom, an olefin polymerization catalyst and a process for producing olefin polymers.

BACKGROUND ART

A number of reports have already been made on the process for producing olefin polymers using a metallocene complex. For example, JP-A-58-19309 discloses a process for producing olefin polymers which uses a metallocene complex and an aluminoxane. The process has a problem in that when olein is polymerized with the disclosed catalyst which uses bis(cyclopentadienyl)zirconium dichloride and methylaluminoxane, the molecular weight of the olefin polymer obtained is low.

The specification of WO87/02370 discloses that the above-mentioned problem is improved by a transition metal complex having a ligand comprising two phenoxy groups linked each other by a sulfur atom. However, the system disclosed in WO87/02370 which uses 2,2'-thiobis(6-tert-butyl-4-methylphenoxy)titanium dichloride and methylaluminoxane and also a system disclosed in JP-A-5-230133 which uses 2,2'-thiobis(6-tert-butyl-4-methylphenoxy) titanium dichloride, triisobutylaluminum and triphenyl-methane tetrakis(pentafluorophenyl)borate involve a problem in that the catalytic activity is unsatisfactorily low from the industrial point of view although the molecular weight of the polymer produced is improved.

JP-A-3-163088 discloses a transition metal complex which has a ligand comprising a cyclopentadienyl ring and an amino group linked thereto by a silicon atom, namely, (tert-butyl-amido)dimethyl(tetramethylcyclopentadienyl) silane zirconium dichloride.

However, no transition metal complex has yet been known which has a ligand comprising a cyclopentadienyl ring and an aromatic ring having oxygen atom in the substituent linked with each other by a sulfur atom or a phosphorus atom.

In recognition of the situation, the objects of the present invention are to provide a transition metal complex useful in industrial process as an olefin polymerization catalyst component which has a ligand comprising an aromatic ring having a hetero atom in the substituent and a cyclopentadienyl ring linked with each other by a hetero atom and to provide a highly active olefin polymerization catalyst and a process for producing olefin polymers.

DISCLOSURE OF THE INVENTION

The present invention relates to a transition metal complex represented by the following formula [1], an olefin polymerization catalyst containing the transition metal complex and a process for producing olefin polymers which uses the catalyst,

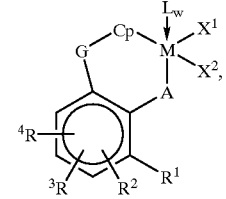

(1)

wherein M is a transition metal atom of the group 4 of the periodic table of elements; Cp is a group having a cyclopentadiene type anionic skeleton; A and G are each a divalent residue containing an atom of the group 15 or 16 of the periodic table of elements and may be the same with or different from each other; $X^1$, $X^2$, $R^1$, $R^2$, $R^3$ and $R^4$ are each independently a hydrogen atom, halogen atom, alkyl group with the number of carbon atoms of 1–20 optionally substituted with at least one halogen atom, aralkyl group with the number of carbon atoms of 7–20 optionally substituted with at least one halogen atom, aryl group with the number of carbon atoms of 6–20 optionally substituted with at least one halogen atom, substituted silyl group with the number of carbon atoms of 1–20 optionally substituted with at least one halogen atom, alkoxy group with the number of carbon atoms of 1–20 optionally substituted with at least one halogen atom, aralkyloxy group with the number of carbon atoms of 7–20 optionally substituted with at least one halogen atom, aryloxy group with the number of carbon atoms of 6–20 optionally substituted with at least one halogen atom or di-substituted amino group with the number of carbon atoms of 2–20, provided that $R^1$, $R^2$, $R^3$ and $R^4$ may optionally combine with each other to form a ring; L is a Lewis base; and w is an integer of 0–2.

(1) Transition metal complex

In the transition metal complex represented by the formula [1] used in the present invention, M is a transition metal atom of the group 4 of the periodic table of elements (Nomenclature of Inorganic Chemistry, IUPAC, revised ed., 1989) and is preferably a titanium, zirconium or hafnium atom.

In the transition metal complex represented by the formula [1], Cp is a group having a cyclopentadiene type anionic skeleton. Specific examples thereof include the cyclpentadienyl group, methylcyclopentadienyl group, dimethylcyclopentadienyl group, trimethylcyclopentadienyl group, tetramethylcyclopentadienyl group, ethylcyclopentadienyl group, n-propylcyclopentadienyl group, isopropylcyclopentadienyl group, n-butylcyclopentadienyl group, sec-butylcyclopentadienyl group, tert-butylcyclopentadienyl group, phenylcyclopentadienyl group, trimethylsilylcyclopentadienyl group, indenyl group, methylindenyl group, dimethylindenyl group, ethylindenyl group, n-propylindenyl group, isopropylindenyl group, n-butylindenyl group, sec-butylindenyl group, tert-butylindenyl group, phenyl-indenyl group, trimethylsilylindenyl group, fluorenyl group, methylfluorenyl group, dimethylfluorenyl group, ethylfluorenyl group, diethylfluorenyl group, n-propylfluorenyl group, di-n-propylfluorenyl group, isopropylfluorenyl group, diisopropylfluorenyl group, n-butylfluorenyl group, di-n-butylfluorenyl group, sec-butylfluorenyl group, di-sec-butylfluorenyl group, tert-butylfluorenyl group, di-tert-butylfluorenyl group, phenylfluorenyl group, diphenylfluorenyl group, trimethylsilylfluorenyl group and ditrimethylsilylfluorenyl group, preferred of these being the cyclopentadienyl group, methylcyclopentadienyl group, tetramethylcyclopentadienyl group, indenyl group, methylindenyl group and fluorenyl group.

In the transition metal complex represented by the formula [1], A and G are each a divalent residue containing an atom of the group 15 or 16 of the periodic table of elements. Such residues may be, for example, divalent groups represented by the following structural formulas and groups resulting from linking the above-mentioned divalent groups with a divalent group of the number of no-hydrogen atoms of 1–20:

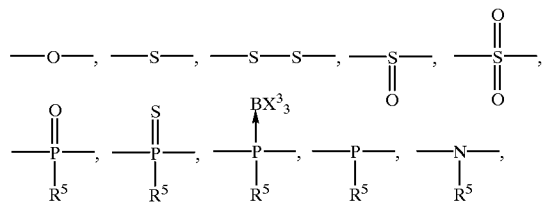

wherein $R^5$ is a halogen atom, hydrocarbon group with the number of carbon atoms of 1–20 or halogenated hydrocarbon group with the number of carbon atoms of 1–20, and is preferably an alkyl group with the number of carbon atoms of 1–20 optionally substituted with at least one halogen atom, aralkyl group with the number of carbon atoms of 7–20 optionally substituted with at least one halogen atom or aryl group with the number of carbon atoms of 6–20 optionally substituted with at least one halogen atom; and $X^3$ is a hydrogen atom or halogen atom.

A is preferably an oxygen atom and G is preferably a divalent group represented by the following structural formula:

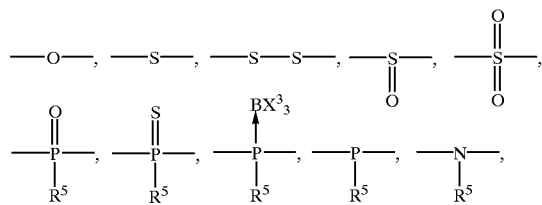

wherein $R^5$ and $X^3$ are the same as defined above.

More preferably, G is a divalent group represented by the following structural formula or a sulfur atom:

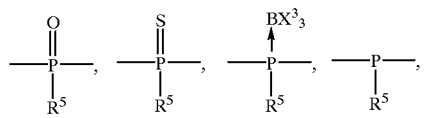

wherein $R^5$ and $X^3$ are the same as defined above.

The halogen atom in $X^1$, $X^2$, $R^1$, $R^2$, $R^3$, $R^4$ and $R^5$ may be a fluorine atom, chlorine atom, bromine atom or iodine atom.

The alkyl group with the number of carbon atoms of 1–20 in $X^1$, $X^2$, $R^1$, $R^2$, $R^3$, $R^4$ and $R^5$ is, for example, the methyl group, ethyl group, n-propyl group, isopropyl group, n-butyl group, sec-butyl group, tert-butyl group, n-pentyl group, neopentyl group, amyl group, n-hexyl group, n-octyl group, n-decyl group, n-dodecyl group, n-pentadecyl group and n-eicosyl group, preferred of these being the methyl group, ethyl group, isopropyl group, tert-butyl group and amyl group.

These alkyl groups may all optionally be substituted with at least one halogen atom (fluorine atom, chlorine atom, bromine atom, iodine atom). The alkyl group with the number of carbon atoms of 1–20 substituted with at least one halogen atom may be, for example, the fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromoethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group and perbromoeicosyl group.

The aralkyl group with the number of carbon atoms of 7–20 in $X^1$, $X^2$, $R^1$, $R^2$, $R^3$, $R^4$ and $R^5$ may be, for example, the benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (4,6-dimethylphenyl)methyl group, (2,3,4-trimethylphenyl)methyl group, (2,3,5-trimethylphenyl)methyl group, (2,3,6-trimethylphenyl) methyl group, (3,4,5-trimethylphenyl)methyl group, (2,4,6-trimethylphenyl)methyl group, (2,3,4,5-tetramethylphenyl) methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl) methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-decylphenyl) methyl group, (n-tetradecylphenyl)methyl group, naphthylmethyl group and anthracenylmethyl group, preferred of these being the benzyl group.

These aralkyl groups may all optionally be substituted with at least one halogen atom (fluorine atom, chlorine atom, bromine atom, iodine atom).

The aryl group with the number of carbon atoms of 6–20 in $X^1$, $X^2$, $R^1$, $R^2$, $R^3$, $R^4$ and $R^5$ may be, for example, the phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group and anthracenyl group, preferred of these being the phenyl group.

These aryl groups may all optionally be substituted with at least one halogen atom (fluorine atom, chlorine atom, bromine atom, iodine atom).

The substituted silyl groups in $X^1$, $X^2$, $R^1$, $R^2$, $R^3$ and $R^4$ refers to a silyl group substituted with at least one hydrocarbon group. The hydrocarbon group may be, for example, an alkyl group with the number of carbon atoms of 1–10, such as methyl group, ethyl group, n-propyl group, isopropyl group, n-butyl group, sec-butyl group, tert-butyl group, isobutyl group, n-pentyl group, n-hexyl group and cyclohexyl group, and an aryl group, such as phenyl group. Such substituted silyl groups with the number of carbon atoms of 1–20 may be, for example, mono-substituted silyl groups with the number of carbon atoms of 1–20, such as methylsilyl group, ethylsilyl group and phenylsilyl group, di-substituted silyl groups with the number of carbon atoms of 2–20, such as dimethylsilyl group, diethylsilyl group and diphenylsilyl group and tri-substituted silyl groups with the number of carbon atoms of 3–20, such as trimethylsilyl group, triethylsilyl group, tri-n-propylsilyl group, triisopropylsilyl group, tri-n-butylsilyl group, tri-sec-butylsilyl group, tri-tert-butylsilyl group, triisobutylsilyl group, tert-butyl-dimethylsilyl group, tri-n-pentylsilyl group, tri-n-hexylsilyl group, tricyclohexylsilyl group and triphenylsilyl group, preferred of these being the trimethylsilyl group, tert-butyldimethylsilyl group and triphenylsilyl group.

These substituted silyl groups may all optionally be substituted with at least one halogen atom (fluorine atom, chlorine atom, bromine atom, iodine atom).

The alkoxy group with the number of carbon atoms of 1–20 in $X^1$, $X^2$, $R^1$, $R^2$, $R^3$ and $R^4$ may be, for example, methoxy group, ethoxy group, n-propoxy group, isopropoxy group, n-butoxy group, sec-butoxy group, tert-butoxy group, n-pentoxy group, neopentoxy group, n-hexoxy group, n-octoxy group, n-dodecoxy group, n-pentadecoxy group, and n-eicosoxy group, and is preferably methoxy group, ethoxy group and tert-butoxy group.

These alkoxy groups may all optionally be substituted with at least one halogen atom (fluorine atom, chlorine atom, bromine atom, iodine atom).

The aralkyloxy group with the number of carbon atoms of 7–20 in $X^1$, $X^2$, $R^1$, $R^2$, $R^3$ and $R^4$ may be, for example, benzyloxy group, (2-methylphenyl)methoxy group, (3-methylphenyl)methoxy group, (4-methylphenyl)methoxy group, (2,3-dimethylphenyl)methoxy group, (2,4-dimethylphenyl)methoxy group, (2,5-dimethylphenyl)methoxy group, (2,6-dimethylphenyl)methoxy group, (3,4-dimethylphenyl)methoxy group, (3,5-dimethylphenyl)methoxy group, (2,3,4-trimethylphenyl)methoxy group, (2,3,5-trimethylphenyl)methoxy group, (2,3,6-trimethylphenyl)methoxy group, (2,4,5-trimethylphenyl)methoxy group, (2,4,6-trimethylphenyl)methoxy group, (3,4,5-trimethylphenyl)methoxy group, (2,3,4,5-tetramethylphenyl)methoxy group, (2,3,4,6-tetramethylphenyl)methoxy group, (2,3,5,6-tetramethylphenyl)methoxy group, (pentamethylphenyl)methoxy group, (ethylphenyl)methoxy group, (n-propylphenyl)methoxy group, (isopropylphenyl)methoxy group, (n-butylphenyl)methoxy group, (sec-butylphenyl)methoxy group, (tert-butylphenyl)methoxy group, (n-hexylphenyl)methoxy group, (n-octylphenyl)methoxy group, (n-decylphenyl)methoxy group, (n-tetradecylphenyl)methoxy group, naphthylmethoxy group and authracenylmethoxy group, and is preferably benzyloxy group.

These aralkyloxy groups may all optionally be substituted with at least one halogen atom (fluorine atom, chlorine atom, bromine atom, iodine atom).

The aryloxy group in $X^1$, $X^2$, $R^1$, $R^2$, $R^3$ and $R^4$ may be, for example, an aryloxy group with the number of carbon atoms of 6–20, such as phenoxy group, 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimthylphenoxy group, 3,4-dimethylphenoxy group, 3,5-dimethylphenoxy group, 2,3,4-trimethylphenoxy group, 2,3,5-trimethylphenoxy group, 2,3,6-trimethylphenoxy group, 2,4,5-trimethylphenoxy group, 2,4,6-trimethylphenoxy group, 3,4,5-trimethylphenoxy group, 2,3,4,5-tetramethylphenoxy group, 2,3,4,6-tetramethylphenoxy group, 2,3,5,6-tetramethylphenoxy group, pentamethylphenoxy group, ethylphenoxy group, n-propylphenoxy group, isopropylphenoxy group, n-butylphenoxy group, sec-butylphenoxy group, tert-butylphenoxy group, n-hexylphenoxy group, n-octylphenoxy group, n-decylphenoxy group, n-tetradecylphenoxy group, naphthoxy group, and anthracenoxy group.

These aryloxy groups may all optionally be substituted with at least one halogen atom (fluorine atom, chlorine atom, bromine atom, iodine atom).

The di-substituted amino group with the number of carbon atoms of 2–20 in $X^1$, $X^2$, $R^1$, $R^2$, $R^3$ and $R^4$ refers to an amino group substituted with two hydrocarbon groups, wherein the hydrocarbon group may be, for example, an alkyl group with the number of carbon atoms of 2–20, such as methyl group, ethyl group, n-propyl group, isopropyl group, n-butyl group, sec-butyl group, tert-butyl group, isobutyl group, n-pentyl group, n-hexyl group and cyclohexyl group, and aryl group, such as phenyl group. Such di-substituted amino group with the number of carbon atoms of 2–20 may be, for example, dimethylamino group, diethylamino group, di-n-propylamino group, diisopropylamino group, di-n-butylamino group, di-sec-butylamino group, di-tert-butylamino group, diisobutylamino group, tert-butylisopropylamino group, di-n-hexylamino group, di-n-octylamino group, di-n-decylamino group, diphenylamino group, bistrimethylsilylamino group and bis-tert-butyldimethylsilylamino group, and is preferably dimethylamino group and diethylamino group.

$R^1$, $R^2$, $R^3$ and $R^4$ may optionally combine with each other to form a ring.

$X^1$ and $X^2$ are each preferably a halogen atom, alkyl group or aralkyl group, more preferably a halogen atom.

Preferred $R^1$ is an alkyl group with the number of carbon atoms of 1–20 optionally substituted with at least one halogen atom, an aralkyl group with the number of carbon atoms of 7–20 optionally substituted with at least one halogen atom, an aryl group with the number of carbon atoms of 6–20 optionally substituted with at least one halogen atom or a substituted silyl group with the number of carbon atoms of 1–20 optionally substituted with at least one halogen atom.

In the transition metal complex represented by the formula [1], L is a Lewis base, specific examples of jwhich include diethyl ether, tetrahydrofuran, dimethylaniline and trimethylphosphine; w is an integer of 0–2.

Specific examples of the complex represented by the formula [1] include thio(cyclopentadienyl)(3-tert-butyl-5-methyl-2-phenoxy)titanium dichloride, thio(methylcyclopentadienyl)(3-tert-butyl-5-methyl-2-phenoxy)titanium dichloride, thio(dimethylcyclopentadienyl)(3-tert-butyl-5-methyl-2-phenoxy)titanium dichloride, thio(trimethylcyclopentadienyl)(3-tert-butyl-5-methyl-2-phenoxy)titanium dichloride, thio (tetramethylcyclopentadienyl)(3-tert-butyl-5-methyl-2-phenoxy)titanium dichloride, thio(ethylcyclopentadienyl)(3-tert-butyl-5-methyl-2-phenoxy)titanium dichloride, thio(n-propylcyclopentadienyl)(3-tert-butyl-5-methyl-2-phenoxy)titanium dichloride, thio(isopropylcyclopentadienyl)(3-tert-butyl-5-methyl-2-phenoxy)titanium dichloride, thio(n-butylcyclopentadienyl)(3-tert-butyl-5-methyl-2-phenoxy)titanium dichloride, thio(sec-butylcyclopentadienyl)(3-tert-butyl-5-methyl-2-phenoxy)titanium dichloride, thio(tert-butylcyclopentadienyl)(3-tert-butyl-5-methyl-2-phenoxy)titanium dichloride, thio(isobutylcyclopentadienyl)(3-tert-butyl-5-methyl-2-phenoxy)titanium dichloride, thio(phenylcyclopentadienyl)(3-tert-butyl-5-methyl-2-phenoxy)titanium dichloride, thio(trimethylsilylcyclopentadienyl)(3-tert-butyl-5-methyl-2-phenoxy)titanium dichloride, thio(indenyl)(3-tert-butyl-5-methyl-2-phenoxy)titanium dichloride, thio(methylindenyl)(3-tert-butyl-5-methyl-2-phenoxy)titanium dichloride, thio(fluorenyl)(3-tert-butyl-5-methyl-2-phenoxy)titanium dichloride, thio(cyclopentadienyl)(3-tert-butyl-2-phenoxy)titanium dichloride, thio(methylcyclopentadienyl)(3-tert-butyl-2-phenoxy)titanium dichloride, thio(dimethylcyclopentadienyl)(3-tert-butyl-2-phenoxy)titanium dichloride, thio(trimethylcyclopentadienyl)(3-tert-butyl-2-phenoxy)titanium dichloride, thio(tetramethylcyclopentadienyl)(3-tert-butyl-2-phenoxy)titanium dichloride, thio(ethylcyclopentadienyl)(3-tert-butyl-2-phenoxy)titanium dichloride, thio(n-propylcyclopentadienyl)(3-tert-butyl-2-phenoxy)titanium dichloride, thio(isopropylcyclopentadienyl)(3-tert-butyl-2-phenoxy)titanium dichloride, thio(n-butylcyclopentadienyl)(3-tert-butyl-2-phenoxy)titanium dichloride, thio(sec-butylcyclopentadienyl)(3-tert-butyl-2-phenoxy)titanium dichloride, thio(tert-butylcyclopentadienyl)(3-tert-butyl-2-phenoxy)titanium dichloride, thio(isobutylcyclopentadienyl)(3-tert-butyl-2-phenoxy)titanium dichloride, thio(phenylcyclopentadienyl)(3-tert-butyl-2-phenoxy)titanium dichloride, thio(trimethylsilylcyclopentadienyl)(3-tert-butyl-2-phenoxy) titanium dichloride, thio(indenyl)(3-tert-butyl-2-phenoxy) titanium dichloride, thio(methylindenyl)(3-tert-butyl-2-phenoxy)titanium dichloride, thio(fluorenyl)(3-tert-butyl-2-phenoxy)titanium dichloride, thio(cyclopentadienyl)(2-phenoxy)titanium dichloride, thio(methylcyclopentadienyl)(2-phenoxy)titanium dichloride, thio(dimethylcyclopentadienyl)(2-phenoxy)titanium dichloride, thio(trimethylcyclopentadienyl)(2-phenoxy)titanium dichloride, thio(tetramethylcyclopentadienyl)(2-phenoxy) titanium dichloride, thio(ethylcyclopentadienyl)(2-phenoxy)titanium dichloride, thio(n-propylcyclopentadienyl)(2-phenoxy)titanium dichloride, thio(isopropylcyclopentadienyl)(2-phenoxy)titanium dichloride, thio(n-butylcyclopentadienyl)(2-phenoxy)titanium dichloride, thio(sec-butylcyclopentadienyl)(2-phenoxy)titanium dichloride, thio(tert-butylcyclopentadienyl)(2-phenoxy)titanium dichloride, thio(isobutylcyclopentadienyl)(2-phenoxy)titanium dichloride, thio(phenylcyclopentadienyl)(2-phenoxy)titanium dichloride, thio(trimethylsilylcyclopentadienyl)(2-phenoxy) titanium dichloride, thio(indenyl)(2-phenoxy)titanium dichloride, thio(methylindenyl)(2-phenoxy)titanium dichloride and thio(fluorenyl)(2-phenoxy)titanium dichloride.

Examples of the transition metal complex also includes compounds resulting from changing "titanium" in the above-mentioned specific examples to zirconium or hafnium; compounds resulting from changing "thio" in the above-mentioned examples, including the compounds newly mentioned above, to oxo, dithio, N-phenylimide, phenyl phosphide, phenylphosphine oxide or phenylphosphine thiooxide; further, compounds resulting from changing "dichloride" to dibromide, dimethyl, diethyl or dibenzyl; and additionally, those compounds in which tetrahydrofuran is coordinately bonded as L in the formula [1] to the above-mentioned compounds.

The transition metal complex represented by the formula [1] can be prepared, for example, by the following methods.

That is, Mg is reacted to a halogenated phenol compound of which phenolic hydroxyl group has been protected with a suitable protective group (e.g., alkoxymethyl group or aralkyl group) to obtain a Grignard reagent. The reagent is then reacted with a dihalogenated phosphorus compound (e.g., phenylphosphonic acid dichloride or phenylphosphine dichloride) and then reacted with an alkali metal salt of a compound having a cyclopentadiene skeleton (e.g., cyclopentadienyllithium or fluorenyllithium) to obtain various compounds comprising the compound having a cyclopentadiene skeleton and the phenol whose hydroxyl group has been protected linked with each other through a phosphorus atom. Further, when the phosphorus atom of the compound thus obtained is coordinately unsaturated, the compound may be reacted with various reagents (e.g., sulfur) to form a compound wherein the phosphorus atom is coordinately saturated (e.g., compounds having a phosphine sulfide group). Then, the protective group is eliminated from the above-mentioned various compounds comprising a cyclopentadiene skeleton and a phenol whose hydroxyl group has been protected linked with each other through a phosphorus atom, by suitable methods (e.g., treatment with aqueous sulfuric acid acidic solution when the protective group is an alkoxymethyl group), then the resulting Cp-phosphorus atom-phenol compound is reacted with 2 equivalents of an alkyllithium (e.g., n-butyllithium), and the reaction product is reacted with a transition metal halide (e.g., titanium tetrachloride), whereby the transition metal complex is obtained.

Alternatively, first a phenol compound is reacted with a sulfurization reagent (e.g., disulfur dichloride) to obtain a dimer bridged with a dithio group. The phenolic hydroxyl group of the dimer is protected with a suitable functional group (e.g., trimethylsilyl group), and then bromine or the like is reacted with the protected compound to sever the sulfur-sulfur bond of the dithio group, and the reaction product is reacted, for example, with an alkali metal salt of a compound having a cyclopentadiene skeleton, to obtain various compounds comprising a compound having a cyclopentadiene skeleton and a phenol compound whose hydroxyl group has been protected linked with each other through sulfur. Then the protective group is eliminated in a suitable manner, the resulting product is reacted with 2 equivalents of an alkyllithium and then reacted with a transition metal halide, whereby the transition metal complex is obtained. In another method, the compound comprising a compound having a cyclopentadiene skeleton and a phenol compound whose hydroxyl group has been protected linked with each other through sulfur is reacted with a transition metal compound capable of reacting with one hydrogen atom of a cyclopentadiene skeleton (e.g., tetrakis(dimethylamido)titanium) to form a Cp-M linkage, and the reaction product is treated with various halogenating agent (e.g., dimethylammonium chloride or hydrogen chloride) several times under varied conditions to eliminate the protective group, whereby a transition metal complex having a cyclic structure containing Cp-M-phenoxy structure is obtained.

(2) Organoaluminum Compound (A)

The compound (A) used in the present invention may be known organoaluminum compounds. Preferred examples thereof include any one compound selected from (A1) an organoaluminum compound represented by the formula $E^1_aAlZ_{3-a}$ and (A2) a cyclic aluminoxane having the structure represented by the formula $\{—Al(E^2)—O—\}_b$ and (A3) a linear aluminoxane having the structure represented by the formula $E^3\{—Al(E^3)—O—\}_cAlE^3_2$ (wherein $E^1$, $E^2$ and $E^3$ are each a hydrocarbon group with the number of carbon atoms of 1–8 and all $E^1$, all $E^2$ and all $E^3$ may be the same with or different from each other; Z is a hydrogen atom or a halogen atom and all Z may be the same with or different from each other; a is the number of 0–3, b is an integer of 2 or more and c is an integer of 1 or more), and mixtures of two or three kinds thereof.

Specific examples of the organoaluminum compound (A1) represented by the formula $E^1_aAlZ_{3-a}$ include trialkylaluminums, such as trimethylaluminum, triethylaluminum, tripropylaluminum, triisobutylaluminum and trihexylaluminum; dialkylaluminum chlorides, such as dimethylaluminum chloride, diethylaluminum chloride, dipropylaluminum chloride, diisobutylaluminum chloride and dihexylaluminum chloride; alkylaluminum dichlorides, such as methylaluminum dichloride, ethylaluminum dichloride, propylaluminum dichloride, isobutylaluminum dichloride, and hexylaluminum dichloride; and dialkylaluminum hydrides, such as dimethylaluminum hydride, diethylaluminum hydride, dipropylaluminum hydride, diisobutylaluminum hydride and dihexylaluminum hydride.

Preferred of these is a trialkylaluminum, more preferred being triethylaluminum and triisobutylaluminum.

Specific examples of $E^2$ and $E^3$ in the cyclic aluminoxane (A2) having the structure represented by the formula $\{—Al(E^2)—O—\}_b$ and the linear aluminoxane (A3) having the structure represented by the formula $E^3\{—Al(E^3)—O—\}_cAlE^3_2$ include alkyl groups, such as methyl, ethyl, n-propyl, isopropyl, n-butyl, isobutyl, n-pentyl and neopentyl; b is an integer of 2 or more and c is an integer of 1 or more. Preferably, $E^2$ and $E^3$ are methyl group and isobutyl group, b is 2–40 and c is 1–40.

The above-mentioned aluminoxanes can be prepared by various methods. There is no particular limitation as to the method, and known methods may be used for preparation. For example, the aluminoxane is prepared by dissolving a trialkylaluminum (e.g., trimethylaluminum) in a suitable organic solvent (e.g., benzene or aliphatic hydrocarbon) and then contacting the resulting solution with water; or it may be prepared by contacting a trialkylaluminum (e.g., trimethylaluminum) with a metal salt containing water of crystallization (e.g., copper sulfate hydrate).

Compound B

The compound used as the compound (B) in the present invention is any one compound selected from (B1) a boron compound represented by the formula $BQ^1Q^2Q^3$ and (B2) a boron compound represented by the formula $J^+(BQ^1Q^2Q^3Q^4)^-$ and (B3) a boron compound represented by the formula $(L—H)^+(BQ^1Q^2Q^3Q^4)^-$.

In the boron compound (B1) represented by the formula $BQ^1Q^2Q^3$, B is a boron atom in the trivalent valence state, and $Q^1-Q^3$ are each a halogen atom, hydrocarbon group containing 1–20 carbon atoms, halogenated hydrocarbon group containing 1–20 carbon atoms, substituted silyl group containing 1–20 carbon atoms, alkoxy group containing 1–20 carbon atoms or di-substituted amino group containing 2–20 carbon atoms, and may be the same with or different from each other. Preferably, $Q^1-Q^3$ are each a halogen atom, hydrocarbon group containing 1–20 carbon atoms or halogenated hydrocarbon group containing 1–20 carbon atoms.

Specific examples of the boron compound (B1) represented by the formula $BQ^1Q^2Q^3$ include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane and phenylbis(pentafluorophenyl)borane, most preferred of these being tris(pentafluorophenyl)borane.

In the boron compound (B2) represented by the formula $J^+(BQ^1Q^2Q^3Q^4)^-$, $J^+$ is an inorganic or organic cation, B is a boron atom in the trivalent valence state, and $Q^1-Q^4$ are the same as defined for $Q^1-Q^3$ in the above-mentioned compound (B1).

As to specific examples of the compound represented by the formula $J^+(BQ^1Q^2Q^3Q^4)^-$, $J^+$ of an inorganic cation is, for example, a ferrocernium cation, alkylsubstituted ferrocenium cation and silver cation and $J^+$ of an organic cation is, for example, a triphenylmethyl cation; $(BQ^1Q^2Q^3Q^4)^-$ is, for example, tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,2,4-trifluorophenyl)borate, phenylbis(pentafluorophenyl)borate and tetrakis(3,5-bistrifluoromethylphenyl)borate.

Examples of the specific combination of these include ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate and triphenylmethyl tetrakis(3,5-bistrifluoromethylphenyl)borate, most preferred of these being triphenylmethyl tetrakis(pentafluorophenyl)borate.

In the boron compound (B3) represented by the formula $(L—H)^+(BQ^1Q^2Q^3Q^4)^-$, L is a neutral Lewis base, $(L—H)^+$ is a Brønsted acid, B is a boron atom in the trivalent valence state, and $Q^1-Q^4$ are the same as defined for $Q^1-Q^3$ in the above-mentioned compound (B1).

In the specific example of the compound represented by the formula $(L—H)^+(BQ^1Q^2Q^3Q^4)^-$, $(L—H)^+$ of the Brønsted acid is, for example, a trialkyl-substituted ammonium, N,N-dialkylanilinium, dialkylammonium and triarylphosphonium, and the $(BQ^1Q^2Q^3Q^4)^-$ may be, for example, the same as those described above.

Examples of specific combination of these include triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate and tri(dimethylphenyl)phosphonium tetrakis(pentafluorophenyl)borate, most preferred of these being tri(n-butyl)ammonium tetrakis(pentafluorophenyl)borate or N,N-dimethylanilinium tetrakis(pentafluorophenyl)borate.

In the present invention, the transition metal complex represented by the formula [1], the compound (A), or further the compound (B) may be charged in any desired order at the time of polymerization. Alternatively, any desired combination of these compounds may be contacted with each other beforehand and the resulting product may be used at the time of polymerization.

As to the amounts of the respective catalyst components, the respective components are desirably used such that the molar ratio of the compound (A) to the transition metal complex may fall within the range of 0.1–10,000, preferably 5–2,000, and the molar ratio of the compound (B) to the transition metal complex may fall within the range of 0.01–100, preferably 0.5–10. With regard to the concentrations of the respective catalyst components when they are used in the form of a solution, the respective components are desirably used such that the concentration of the transition metal complex represented by the formula [1] may fall within the range of 0.0001–5 mmol/l, preferably 0.001–1 mmol/l, the concentration of the compound (A) in terms of Al atom within the range of 0.01–500 mmol/l, preferably 0.1–100 mmol/l and the compound (B) within the range of 0.0001–5 mmol/l, preferably 0.001–1 mmol/l.

In the present invention, the monomer used for polymerization may be any of the olefins and diolefins each with the number of carbon atoms of 2–20. Two or more kinds of monomers may also be used simultaneously. Specific examples of the monomers include ethylene, propylene, butene-1, pentene-1, hexene-1 heptene-1, octene-1, nonene-1, decene-1, 5-methyl-2-pentene-1 and vinylcyclohexene, but the present invention is not to be limited to these compounds. Specific examples of the monomers which constitute copolymers include the combination of ethylene and propylene, ethylene and butene-1, ethylene and hexene-1, and propylene and butene-1, but the present invention is not to be limited to these compounds.

The method of polymerization also is not particularly limited. There may be used, for example, solvent polymerization or slurry polymerization wherein aliphatic hydrocarbons, such as butane, pentane, hexane, heptane and octane, aromatic hydrocarbons, such as benzene and toluene, or halogenated hydrocarbons, such as methylene dichloride, are used as the solvent, and gas phase polymerization conducted in gaseous monomers, or high pressure polymerization in which the monomer is in the supercritical state at high temperature and high pressure. Further, polymerization may be conducted either continuously or batch-wise.

The polymerization temperature may be in the range from −50° C. to +300° C., but it is particularly preferably in the range from −20° C. to +250° C. The polymerization pressure may be in the range from normal pressure to 2,000 kg/cm$^2$G, preferably in the range from normal pressure to 1,000 kg/cm$^2$G. The polymerization time, in general, is determined according to the kind of intended polymer and the reaction apparatus, and may be in the range from 1 minute to 20 hours. In the present invention, chain transfer agents, such as hydrogen, may be added to control the molecular weight of the copolymer.

BEST MODE FOR CARRYING OUT THE INVENTION

The present invention is described below in detail with reference to Examples, but the invention is not limited thereto.

The properties of polymers shown in Examples were determined by the following methods.
(1) Intrinsic viscosity [η]: The intrinsic viscosity was determined by using an Ubbelohde viscometer with a tetralin solution at 130° C.
(2) α-Olefin content: The α-olefin content was determined from the characteristic absorptions of ethylene and a-olefin by using an infrared spectrophotometer (IR-810, mfd. by Nippon Bunko Kogyo K.K.) and was expressed in terms of the number of short chain branching (SCB) per 1,000 carbon atoms.
(3) Melting point of copolymer: The melting point was determined by using Seiko-SSC-5200 under the following conditions.
  Temperature increase: from −40° C. to 150° C. (10° C./min), kept for 5 minutes
  Cooling: from 150° C. to 10° C. (5° C./min), kept for 10 minutes
  Determination: from 10° C. to 160° C. (5° C./min)

EXAMPLE 1

(1) Synthesis of transition metal complex
(1-1) Synthesis of 2-bromo-4-methyl-6-tert-butylphenol Under nitrogen atmosphere, a dimethylformamide 100 ml solution of N-bromosuccinimide (22.25 g, 125 mmol) was added dropwise at 0° C. to a dimethylformamide 100 ml solution of 2-tert-butyl-4-methylphenol (20.53 g, 125 mmol) with stirring, the resulting reaction mixture was brought up to room temperature and stirred for 5 hours.

The solvent was removed from the reaction mixture under reduced pressure, then 200 ml of water was added to the residue, and the resulting mixture was extracted with ethyl acetate (extracted twice with 200 ml of ethyl acetate). The organic solution layers were combined, washed with 100 ml of saturated aqueous sodium chloride solution, then dried with anhydrous magnesium sulfate, and the solvent was removed. The residue was purified by silica gel column chromatography to obtain an oily product. The $^1$H-NMR spectrum data of the product are shown below. The NMR data were obtained by determination with EX-270 (mfd. by JEOL).

$^1$H-NMR (CDCl$_3$, 270 MHz) δ: 1.39 (s, 9H), 2.25 (s, 3H), 5.62 (s, 1H), 7.00 (s, 1H), 7.15 (s, 1H)
(1-2) Synthesis of 1-bromo-2-methoxymethyloxy-3-tert-butyl-5-methylbenzene Under nitrogen atmosphere, a THF 50 ml solution of 2-bromo-4-methyl-6-tert-butylphenol(23.41 g, 100 mmol) was added dropwise at 0° C. with stirring to a 100 ml THF suspension of sodium hydride (60%, 5.20 g, 130 mmol). After 2 hours, a THF 20 ml solution of methoxymethyl chloride (95%, 12.71 g, 150 mmol) was added dropwise to the mixture obtained above, the resulting mixture was brought up to room temperature and stirred for 10 hours. The reaction liquid thus obtained was cooled to 0° C., 100 ml of water was added thereto, and the aqueous layer was extracted with toluene (extracted twice with 200 ml of toluene). The organic solution layers were combined, washed with 100 ml of saturated aqueous sodium chloride solution, then dried with anhydrous sodium sulfate and the solvent was removed. The residue was purified by silica gel column chromatography to obtain a colorless oil. The $^1$H-NMR spectrum data of the oil are shown below. The NMR data were determined by using EX-270 (mfd. by JEOL).

$^1$H-NMR (CDCl$_3$, 270 MHz) δ: 1.41 (s, 9H), 2.27 (s, 3H), 3.68 (s, 3H), 5.20 (s, 2H), 7.08 (d, 1H, J=2Hz), 7.24 (d, 1H, J=2Hz)
(1-3) Synthesis of 3-tert-butyl-2-methoxymethyloxy-5-methylphenylmagnesium bromide Under nitrogen atmosphere, a THF 30 ml solution of 1-bromo-2-methoxymethyloxy-3-tert-butyl-5-methylbenzene (4.31 g, 15 mmol) was added dropwise at room temperature to a tetrahydrofuran 50 ml slurry containing 0.37 g (15 mmol) of magnesium and 0.001 mg of iodine and, after completion of the dropwise addition, the reaction mixture was refluxed for 1 hour to obtain a 50 ml THF solution of 3-tert-butyl-2-methoxymethyloxy-5-methylphenylmagnesium bromide (15 mmol).

(1-4) Synthesis of (3-tert-butyl-2-methoxymethyloxy-5-methylphenyl)(fluoren-9-yl)phenylphosphine oxide Under nitrogen atmosphere, a 50 ml THF solution of 3-tert-butyl-2-methoxymethyloxy-5-methylphenylmagnesium bromide (15 mmol) was added dropwise at −78° C. with stirring to a THF 50 ml solution of phenylphosphonic acid dichloride (2.92 g, 15 mmol), and the resulting mixture was brought up to room temperature and stirred for 2 hours. The resulting solution was cooled to −78° C., a 50 ml THF solution of 9-fluorenyllithium (15 mmol) was added dropwise thereto, the mixture was brought up to room temperature and then stirred for 12 hours. Then 50 ml of a saturated aqueous ammonium chloride solution was added to stop the reaction. The organic layer was separated, and the aqueous layer was extracted with toluene (extracted twice with 50 ml of toluene). The organic layers were combined, washed with 50 ml of saturated aqueous sodium chloride solution, dried with anhydrous magnesium chloride and then the solvent was removed. The residue was purified by silica gel column chromatography to obtain 0.55 g of yellowish white crystals.

$^1$H-NMR (CDCl$_3$, 270 MHz) δ: 1.58 (s, 9H), 2.19 (s, 3H), 3.75 (s, 3H), 5.22 (d, 1H, J=4Hz), 5.76 (d, 1H, J=27Hz), 6.24 (d, 1H, J=4Hz), 6.72 (d, 2H, J=8Hz), 6.76 (dd, 2H, J=12, 1Hz), 6.92 (dt, 2H, J=8.3Hz), 7.05 (dd, 1H, J=8, 7Hz), 7.2–7.4 (m, 4H), 7.45 (dd, 2H, J=12, 2Hz), 7.57 (d, 1H, J=8Hz), 8.11 (dd, 1H, J=7, 2Hz) m.p. 234–236° C.

From the above data, the yellowish white crystal obtained was identified as (3-tert-butyl-2-methoxymethyloxy-5-methylphenyl)(fluoren-9-yl)phenylphosphine oxide of the following structural formula.

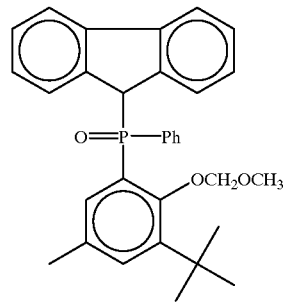

(1-5) Synthesis of (3-tert-butyl-2-hydroxy-5-methylphenyl)(fluoren-9-yl)phenylphosphine oxide (3-tert-Butyl-2-methoxymethyloxy-5-methylphenyl)(fluoren-9-yl)phenylphosphine oxide (1.7 g) was dissolved in chloroform (100 ml), then a mixed solution of methanol (10 ml), water (10 ml) and sulfuric acid (1 ml) was added thereto, and the resulting mixture was stirred at room temperature for 8 hours.

Thereafter, the mixture was neutralized by addition of a 10% aqueous sodium hydroxide solution, then the solvent was distilled off under reduced pressure, water (150 ml) was added to the residue obtained, and the resulting mixture was subjected twice to extraction treatment using chloroform (10 ml). The organic layer obtained was combined, dried with anhydrous magnesium sulfate and then the solvent was distilled off.

The residue obtained was treated by silica gel column chromatography to obtain 1.31 g of (3-tert-butyl-2-hydroxy-5-methylphenyl)(fluoren-9-yl)phenylphosphine oxide of the following structural formula.

$^1$H-NMR (CDCl$_3$, 270 MHz) δ: 1.25 (s, 9H), 1.92 (s, 3H), 5.11 (d, 1H, J=20Hz), 5.89 (dd, 1H, J=13, 2Hz), 6.78 (dd, 1H, J=8, 1Hz), 7.02 (d, 1H, J=2Hz), 7.07 (ddd, 1H, J=8, 8, 1Hz), 7.21 (ddd, 1H, J=8, 8, 1Hz), 7.33 (ddd, 2H, J=7, 7, 7Hz), 7.5–7.6 (m, 3H), 7.66 (ddd, 3H, J=7, 7, 7Hz), 7.82 (dd, 1H, J=11, 2), 7.85 (dddd, 1H, J=11, 1, 1, 1Hz), 11.14 (s, 1H). m.p. 237–240° C.

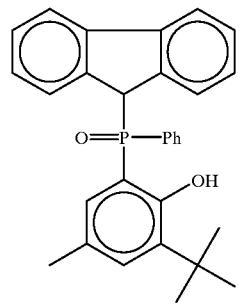

(1-6) Synthesis of phenylphosphine oxide (fluorenyl)(3-tert-butyl-5-methyl-2-phenoxy)(tetrahydrofuran)titanium dichloride A 1.72 mol/l hexane solution of n-butyllithium (0.6 ml, 1 mmol) was added dropwise at 0° C. with stirring to a diethyl ether 20 ml solution of (3-tert-butyl-2-hydroxy-5-methylphenyl)(fluoren-9-yl)phenylphosphine oxide (0.226 g, 0.5 mmol), the resulting mixture was gradually brought up to room temperature and further stirred for 12 hours. The white precipitate thus formed was collected by filtration and washed with diethyl ether to obtain white powder. Then 10 ml of THF was added to the powder to form a THF solution of phenylphosphine oxide (fluorenyl)(3-tert-butyl-5-methyl-2-phenoxy)dilithium.

In a separate reaction vessel, a 1 mol/l toluene solution of titanium tetrachloride (0.5 ml, 0.5 mmol) was added to 10 ml of frozen (−196° C.) THF. The resulting mixture was brought up to −78° C. to obtain a yellow solution. To the solution was added dropwise the above-mentioned THF solution of phenylphosphine oxide (fluorenyl)(3-tert-butyl-5-methyl-2-phenoxy)dilithium, the resulting solution was brought up to room temperature while being stirred for 12 hours.

The solvent was removed from the deep red solution thus formed, and the residue was extracted with toluene. The mother liquor was concentrated, then 10 ml of n-hexane was added thereto, the precipitate thus formed was collected by filtration and washed with n-hexane to obtain 0.10 g of orange powder. The $^1$H-NMR spectrum data of the powder are shown below. The NMR data were determined by using EX-270 (mfd. by JEOL).

$^1$H-NMR (C$_6$D$_6$, 270 MHz) δ: 1.42 (m, 4H), 1.80 (s, 9H), 2.02 (m, 3H), 4.10 (m, 4H), 5.75 (d, 1H, J=26Hz), 6.31 (dd, 1H, J=12, 1Hz), 6.70–7.16 (m, 4H), 7.69 (dd, 1H, J=7, 1Hz)

From the $^1$H-NMR data, the orange powder obtained was identified as phenylphosphine oxide (fluorenyl)(3-tert-butyl-5-methyl-2-phenoxy)(tetrahydrofuran)titanium dichloride. The yield was 32%.

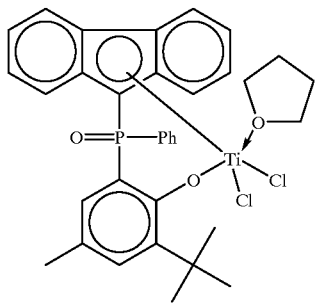

(2) Polymerization

An autoclave with an inner volume of 0.4 l fitted with a stirrer was dried under reduced pressure and the inner atmosphere was replaced with argon. Then 170 ml of toluene as the solvent and 30 ml of hexene-1 as the α-olefin were placed therein, and the reactor was brought up to 80° C. After the temperature rise, ethylene was fed into the reactor while the ethylene pressure being controlled at 12 kg/cm². After the inside of the system had become stable, 1.0 mmol of triisobutylaluminum, then 5.0 μmol of phenylphosphine oxide (fluorenyl)(3-tert-butyl-5-methyl-2-phenoxy)(tetrahydrofuran)titanium dichloride synthesized in (1) above, and then 15.0 μmol of triphenylmethyl tetrakis(pentafluorophenyl)borate were successively charged into the reactor. Polymerization was carried out for 30 minutes while controlling the temperature at 80° C.

As the result of polymerization, an ethylenehexene-1 copolymer having an SCB of 14.3, [η] of 6.69 and melting point of 117.10° C. was produced at a rate of 5.72×10⁵ g per mol of titanium per hour.

Comparative Example 1
(1) Polymerization

An autoclave with an inner volume of 400 ml fitted with a stirrer was dried under reduced pressure and the inner atmosphere was replaced with argon. Then, 170 ml of toluene as the solvent and 30 ml of hexene-1 as the α-olefin were placed therein and the reactor was brought up to 80° C. After the temperature rise, ethylene was fed into the reactor while the ethylene pressure being controlled at 6 kg/cm². After the inside of the system had become stable, 0.25 mmol of triethylaluminum, then 5.0 μmol of 2,2'-thiobis(6-tert-butyl-4-methylphenoxy)titanium dichloride synthesized according to the method described in WO87/02370 and JP-A-5-230133, and then 15.0 μmol of triphenylmethyl tetrakis(pentafluorophenyl)borate were successively charged into the reactor. Polymerization was carried out for 60 minutes while controlling the temperature at 80° C.

As the result of polymerization, an ethylene hexene-1 copolymer having an SCB of 26.1, [η] of 3.78, and melting point of 116.8° C. was produced at a rate of 2.9×104 g per mol of titanium.

EXAMPLE 2
(1-1) Synthesis of bis(3-tert-butyl-5-methyl-2-phenol)-1-disulfide

Under nitrogen atmosphere, in a Schlenk tube fitted with a stirrer, 8.49 g (26.3 mmol) of disulfur dichloride was dissolved in 40 ml of hexane. To the solution was added 20 ml of a hexane solution of 18.49 g (51.8 mmol) of 2-tert-butyl-p-cresol with ice-cooling over 30 minutes, and the resulting mixture was stirred at room temperature for 6 hours. Then the solvent was distilled off under reduced pressure to obtain 10.62 g of a yellow solid. The solid was dissolved in 20 ml of hexane, and the solution was cooled to separate into a precipitated pale yellow solid and a yellow solution. The yellow solution was collected by separation, and the solvent was distilled off therefrom under reduced pressure to obtain 8.4 g of a yellow solid. The yellow solid was purified by developing on a silica gel column (Silica gel 60, Merck Ltd.) with a hexane-benzene mixed solution (hexane: benzene=5:1) and removing the solvent from the resulting fraction, to obtain 3.47 g of a yellow solid. The ¹H-NMR (CDCl₃ solvent) data of the solid are shown below. The NMR data were determined by using AC-200 (200 MHz) (mfd. by Bruker Ltd.).

δ: 1.37 (s, 9H), 2.19 (s, 3H), 6.53 (s, 1H), 6.99 (d, 1H), 7.11 (d, 1H).

Additionally, the ¹³C-NMR (CDCl₃ solvent) data are shown below.

δ: 20.51, 29.38, 35.03, 120.63, 129.07, 131.39, 133.92, 136.31, 153.20

From the ¹H- and ¹³C-NMR data, the yellow solid obtained was identified as bis(3-tert-butyl-5-methyl-2-phenol)-1-disulfide of the following structural formula. The yield was 34.4%.

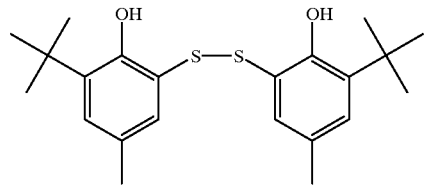

(1-2) Synthesis of bis(3-tert-butyl-5-methyl-2-phenol-trimethylsilyl ether)-1-disulfide Under nitrogen atmosphere, in a Schlenk tube fitted with a stirrer, 3.33 g (8.45 mmol) of bis(3-tert-butyl-5-methyl-2-phenol)-1-disulfide was dissolved in 30 ml of THF, then 2.20 ml (17.4 mmol) of chlorotrimethylsilane was added thereto, and the resulting mixture was ice-cooled. Thereto was further added 2.4 ml (17.2 mmol) of triethylamine, the resulting mixture was gradually brought back to room temperature and stirred at room temperature for 2 hours. After the mixed had become a pale yellow suspension, the solvent was distilled off under reduced pressure to obtain a pale yellow solid. The pale yellow solid was dissolved in 50 ml of ether, the resulting solution was washed twice with 20 ml of distilled water and once with 20 ml of saturated aqueous sodium chloride solution, then dried with anhydrous sodium sulfate for 2 hours and filtered. The filtrate was stripped of the solvent under reduced pressure to obtain 4.31 g of a yellow solid. The ¹H-NMR (CDCl₃ solvent) data of the solid are shown below. The NMR data were determined by using AC-200 (200 MHz) (mfd. by Bruker Ltd.).

δ: 0.37 (s, 9H), 1.36 (s, 9H), 2.19 (s, 3H), 7.04 (d, 1H), 7.10 (d, 1H).

From these ¹H-NMR data, the yellow solid obtained was identified as bis(3-tert-butyl-5-methyl-2-phenol-trimethylsilyl ether)-disulfide of the following structural formula. The yield was 94.5%.

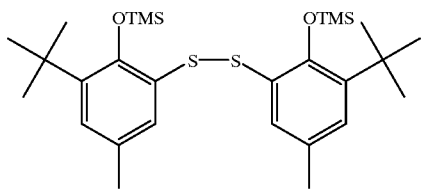

(1-3) Synthesis of 3-tert-butyl-5-methyl-thiocyclopentadienyl-2-phenol trimethylsilyl ether Under nitrogen atmosphere, in a Schlenk tube fitted with a stirrer, 388.9 g (0.728 mmol) of bis(3-tert-butyl-5-methyl-2-phenol-trimethylsilyl ether)-1-disulfide was dissolved in 1.0 ml of methylene chloride, and 123.3 mg (0.772 mmol) of bromine was added thereto, whereby 3-tert-butyl-5-methyl-2-phenol-trimethylsilyl ether-1-sulfenyl bromide was formed. The solution obtained above was added by portions at −50° C. to 2 ml of a THF solution of 194.4 mg (2.21 mmol) of cyclopentadienylsodium. The resulting mixture was brought back slowly to room temperature and stirred at room temperature for 5 hours. Then the solvent was distilled off under reduced pressure to obtain 620.7 mg of a liver brown solid. The solid was dissolved in 30 ml of methylene chloride, the resulting solution was filtered, and the solvent of the filtrate was distilled off under reduced pressure to obtain 518.2 mg of a liver brown solid. The solid was purified by applying it to a silica gel column (Silica gel 60, mfd. by Merck Ltd.), followed by developing with a hexane-benzene mixed solvent (hexane:benzene=5:1), and then removing the solvent of the fraction obtained under reduced pressure, to obtain 26.5 mg of a red solid. The $^1$H-NMR (CDCl$_3$ solvent) data of the solid are shown below.

The NMR data were determined by using AC-200 (200 MHz) mfd. by Bruker Ltd.

δ: 0.365 (s, 9H), 1.38 (s, 9H), 2.23 (s, 3H), 2.93 (m, 1H), 3.06 (m, 1H), 5.99–6.19 (m, 1H), 6.29 (m, 1H), 6.43 (m, 1H), 7.07 (br, 2H).

From the $^1$H-NMR data, the red solid obtained was identified as 3-tert-butyl-5-methyl-thiocyclopentadienyl-2-phenol trimethylsilyl ether of the following structural formula. The yield was 7.0%.

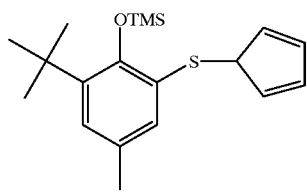

(1-4) Synthesis of (6-tert-butyl-4-methyl-2-trimethylsiloxy-phenylthio)(cyclopentadienyl)(trisdimethylamido)titanium In a Schlenk tube fitted with a stirrer, 50 mg (0.223 mmol) of tetrakis(dimethylamido)titanium and 54.5 mg (0.164 mmol) of 3-tert-butyl-5-methyl-thiocyclopentadienyl-2-phenol trimethylsilyl ether were added to 8 ml of toluene, and then 8 ml of toluene was transferred thereto under vacuum. The resulting solution was stirred at 50° C. for 2 hours and at room temperature for 4 hours. Thereafter, the solvent of the solution was distilled off under reduced pressure to obtain 95 mg of brown tar. The $^1$H-NMR (C$_6$D$_6$ solvent) of the tar was determined by using AC-200 (200 MHz) mfd. by Bruker Ltd. The NMR data thus obtained are shown below.

δ: 0.575 (s, 9H), 1.46 (s, 9H), 2.05 (s, 3H), 3.14 (s, 18H), 5.94 (t, 2H), 6.14 (t, 2H), 6.86 (d, 1H), 6.99 (d, 1H).

From the $^1$H-NMR data, the tar obtained above was identified as (6-tert-butyl-4-methyl-2-trimethylsiloxy-phenylthio)(cyclopentadienyl)(tris-dimethylamido)titanium of the following structural formula. The yield was 100%.

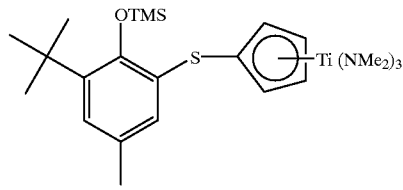

(1-5) Synthesis of (6-tert-butyl-4-methyl-2-trimethylsiloxy-phenylthio)(cyclopentadienyl)(dimethylamido)titanium dichloride In a Schlenk tube fitted with a stirrer were placed 270 mg (0.505 mmol) of (6-tert-butyl-4-methyl-2-trimethylsiloxy-phenylthio)(cyclopentadienyl)(trisdimethylamido)titanium and 123 mg (1.51 mmol) of dimethylammonium chloride, and then 8 ml of dichloromethane was transferred thereto under vacuum. The resulting solution was stirred at −20° C. for 4 hours and at room temperature for 2 hours. Thereafter, the solvent was distilled off under reduced pressure to obtain 303 mg of brown tar. The $^1$H-NMR (CDCl$_3$ solvent) of the tar was determined by using AC-200 (200 MHz) mfd. by Bruker Ltd. The data thus obtained are shown below.

δ: 0.324 (s, 9H), 1.37 (s, 9H), 2.24 (s, 3H), 6.17 (t, 2H), 6.51 (t, 2H), 7.17 (d, 1H), 7.28 (d, 1H).

From the $^1$H-NMR data, the tar obtained above was identified as (6-tert-butyl-4-methyl-2-trimethylsiloxy-phenylthio)(cyclopentadienyl)(dimethylamido)titanium dichloride of the following structural formula. The yield was 100%.

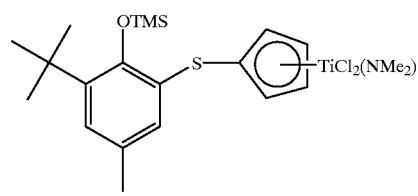

(1-6) Synthesis of (6-tert-butyl-4-methyl-2-trimethylsiloxy-phenylthio)(cyclopentadienyl)titanium trichloride To 15 ml of chloroform containing dried hydrogen chloride placed in a Schlenk tube fitted with a stirrer was added at 0° C. 270 mg (0.505 mmol) of (6-tert-butyl-4-methyl-2-trimethylsiloxy-phenylthio)(cyclopentadienyl)(dimethylamido)titanium dichloride. The resulting solution was stirred at 0° C. for 30 minutes and at room temperature for 2 hours. The resulting suspension was filtered by using Celite. Thereafter the solvent was distilled off under reduced pressure to obtain 303 mg of brown tar. The $^1$H-NMR (CDCl$_3$ solvent) of the tar was determined by using AC-200 (200 MHz) mfd. by Bruker Ltd. The data thus obtained are shown below.

δ: 1.40 (s, 9H), 2.31 (s, 3H), 3.88 (s, 3H), 6.67 (t, 2H), 6.78 (t, 2H), 7.26 (d, 1H), 7.31 (d, 1H).

From $^1$H-NMR data, the tar obtained above was identified as (6-tert-butyl-4-methyl-2-trimethylsiloxyphenylthio)(cyctopentadienyl)titanium trichloride of the following structural formula. The yield was 100%.

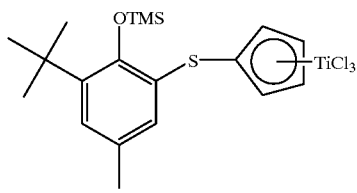

(1-7) Synthesis of thio(cyclopentadienyl)(6-tert-butyl-4-methyl-2-phenoxy)titanium dichloride To 15 ml of diethyl ether containing dried hydrogen chloride placed in a Schlenk tube fitted with a stirrer was added at 0° C. 88.4 mg (0.182 mmol) of (6-tert-butyl-4-methyl-2-trimethylsiloxy-phenylthio)(cyclopentadienyl) titanium trichloride. The resulting solution was stirred at 0° C. for 1 minute and at room temperature for 16 hours. The resulting suspension was filtered by using Celite. Thereafter, the solvent was distilled off under reduced pressure to obtain 46.0 mg of brown tar. The $^1$H-NMR (CDCl$_3$ solvent) of the tar was determined by using AC-200 (200 MHz) mfd. by Bruker Ltd. The data thus obtained are shown below.

δ: 1.45 (s, 9H), 2.25 (s, 3H), 6.17 (t, 2H), 6.92 (t, 2H), 7.21 (d, 1H), 7.26 (d, 1H).

From the $^1$H-NMR data, the tar obtained above was identified as (thio(cyclopentadienyl)(6-tert-butyl-4-methyl-2-phenoxy)titanium dichloride of the following structural formula. The yield was 67.0%.

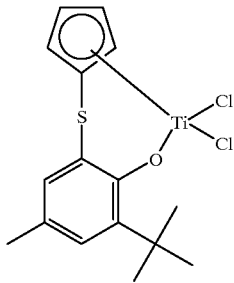

(2) Polymerization

By polymerizing ethylene with hexene-1 in the same manner as in Example 1(2), an ethylene-hexene-1 copolymer can be obtained.

INDUSTRIAL APPLICABILITY

As set forth above, according to the present invention, a transition mental complex useful as an olefin polymerization catalyst component in industrial processes which has a ligand comprising an aromatic ring having a hetero atom of the group 15 or 16 in the substituent and a cyclopentadienyl ring linked with each other through a divalent residue containing an atom of the group 15 or 16 is provided. Further, by using a catalyst containing the complex, olefin polymers, particularly linear low density polyethylene, having a high molecular weight and narrow composition distribution can be produced with good efficiency.

We claim:

1. A transition metal complex represented by the formula [1]

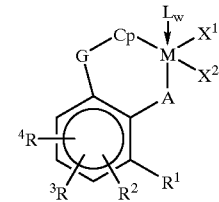

wherein M is a transition metal atom of the group 4 of the periodic table of elements; Cp is a group having a cyclopentadiene containing anionic skeleton; A and G are each a divalent residue containing an atom of the group 15 or 16 of the periodic table of elements and may be the same with or different from each other; $X^1$, $X^2$, $R^1$, $R^2$, $R^3$ and $R^4$ are each independently a hydrogen atom, halogen atom, alkyl group with the number of carbon atoms of 1–20 optionally substituted with at least one halogen atom, aralkyl group with the number of carbon atoms of 7–20 optionally substituted with at least one halogen atom, aryl group with the number of carbon atoms of 6–20 optionally substituted with at least one halogen atom, substituted silyl group with the number of carbon atoms of 1–20 optionally substituted with at least one halogen atom, alkoxy group with the number of carbon atoms of 1–20 optionally substituted with at least one halogen atom, aralkyloxy group with the number of carbon atoms of 7–20 optionally substituted with at least one halogen atom, aryloxy group with the number of carbon atoms of 6–20 optionally substituted with at least one halogen atom, or di-substituted amino group with the number of carbon atoms of 2–20, provided that $R^1$, $R^2$, $R^3$ and $R^4$ may optionally combine with each other to form a ring; L is a Lewis base; and w is an integer of 0–2.

2. The transition metal complex according to claim 1 wherein M in the transition metal complex represented by the formula [1] is a titanium atom.

3. The transition metal complex according to claim 1 wherein A and G in the transition metal complex represented by the formula [1] are each independently represented by any of the following structural formulas

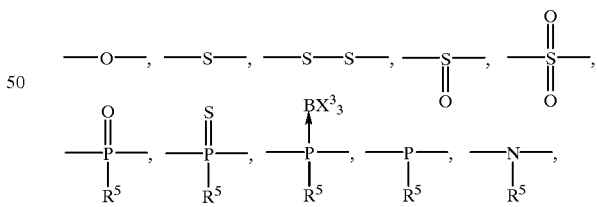

wherein $R^5$ is a halogen atom, hydrocarbon group with the number of carbon atoms of 1–20 or halogenated hydrocarbon group with the number of carbon atoms of 1–20, and $X^3$ is a hydrogen atom or halogen atom.

4. The transition metal complex according to claim 1 wherein A in the transition metal complex represented by the formula [1] is an oxygen atom.

5. The transition metal complex according to claim 1 wherein G in the transition metal complex represented by the formula [1] is represented by any of the following structural formulas

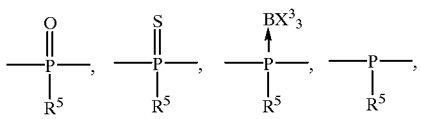

wherein $R^5$ is a halogen atom, hydrocarbon group with the number of carbon atoms of 1–20 or halogenated hydrocarbon group with the number of carbon atoms of 1–20, and $X^3$ is a hydrogen atom or halogen atom.

6. The transition metal complex according to claim 1 wherein G in the transition metal complex represented by the formula [1] is a sulfur atom.

7. The transition metal complex according to claim 1 wherein $R^1$ in the transition metal complex represented by the formula [1] is a hydrocarbon group with the number of carbon atoms of 1–20 or halogenated hydrocarbon group with the number of carbon atoms of 1–20.

8. The transition metal complex according to claim 1 wherein $X^1$ and $X^2$ in the transition metal complex represented by the formula [1] are each a halogen atom.

9. An olefin polymerization catalyst which comprises the transition metal complex according to claim 1 and a compound (A) described below:

(A) any one of the following compounds (A1)–(A3) or a mixture of two or three thereof,
(A1) an organoaluminum compound represented by the formula $E^1{}_a AlZ_{3-a}$
(A2) a cyclic aluminoxane having the structure represented by the formula $\{—Al(E^2)—O—\}_b$
(A3) a linear aluminoxane having the structure represented by the formula $E^3\{—Al(E^3)—O—\}_c AlE^3{}_2$
wherein $E^1$–$E^3$ are each a hydrocarbon group with the number of carbon atoms of 1–8 and all $E^1$, all $E^2$ and all $E^3$ may be the same with or different from each other; Z is a hydrogen atom or halogen atom, and all Z may be the same with or different from each other; a is an integer of 0–3, b is an integer of 2 or more, and c is an integer of 1 or more.

10. An olefin polymerization catalyst which comprises the transition metal complex according to claim 1 and the following compounds (A) and (B):

(A) any one of the following compounds (A₁)–(A3) or a mixture of two or three thereof,
(A1) an organoaluminum compound represented by the formula $E^1{}_a AlZ_{3-a}$
(A2) a cyclic aluminoxane having the structure represented by the formula $\{—Al(E^2)—O—\}_b$
(A3) a linear aluminoxane having the structure represented by the formula $E^3\{—Al(E^3)—O—\}_c AlE^3{}_2$
wherein $E^1$–$E^3$ are each a hydrocarbon group with the number of carbon atoms of 1–8 and all $E^1$, all $E^2$ and all $E^3$ may be the same with or different from each other; Z is a hydrogen atom or halogen atom and all Z may be the same with or different from each other; a is an interges of 0–3, b is an integer of 2 or more, and c is an integer of 1 or more.

(B) any of the following compounds (B1)–(B3):
(B1) a boron compound represented by the formula $BQ^1Q^2Q^3$
(B2) a boron compound represented by the formula $J^+(BQ^1Q^2Q^3Q^4)^-$
(B3) a boron compound represented by the formula $(L—H)^+(BQ^1Q^2Q^3Q^4)^-$ wherein B is a boron atom in the trivalent valence state; $Q^1$–$Q^4$ are each a halogen atom, hydrocarbon group with the number of carbon atoms of 1–20, halogenated hydrocarbon group with the number of carbon atoms of 1–20, substituted silyl group with the number of carbon atoms of 1–20, alkoxy group with the number of carbon atoms of 1–20 or di-substituted amino group with the number of carbon atoms of 2–20, and may be the same with or different from each other; $J^+$ is an inorganic or organic cation, L is a neutral Lewis base and $(L—H)^+$ is a Brønsted acid.

11. The olefin polymerization catalyst according to claim 9 or 10 wherein the compound (A) is triethylaluminum, triisobutylaluminum or methylaluminoxane.

12. A process for producing an olefin polymer which comprises polymerizing at least one olefin in the presence of the olefin polymerization catalyst according to any of claims 9–11.

13. The process for producing an olefin polymer according to claim 12 wherein the olefin polymer is an ethylene-α-olefin copolymer.

14. The transition metal complex according to claim 1 wherein M in the transition metal complex ropresented by the formula [1] is a zirconium atom.

15. The transition metal complex according to claim 1 wherein M in the transition metal complex represented by the formula [1] is a hafnium atom.

* * * * *